United States Patent [19]

Milman

[11] Patent Number: 4,973,250
[45] Date of Patent: Nov. 27, 1990

[54] APPARATUS AND METHOD FOR IRRIGATING AND ASPIRATING PERIODONTAL POCKETS

[76] Inventor: Anita S. Milman, 620 S. Sweetzer Ave., Los Angeles, Calif. 90048

[21] Appl. No.: 322,785

[22] Filed: Mar. 13, 1989

[51] Int. Cl.⁵ ............................................. A61C 5/00
[52] U.S. Cl. ...................................... 433/215; 433/80
[58] Field of Search ..................... 433/80, 89, 215; 128/66; 604/212, 216, 204

[56] References Cited

U.S. PATENT DOCUMENTS

| 169,384 | 11/1875 | Starr | 604/212 X |
|---|---|---|---|
| 1,488,777 | 4/1924 | Clements | 604/212 X |
| 1,762,237 | 6/1930 | Moore | 604/212 |
| 2,029,483 | 2/1936 | Holland | 604/212 |
| 2,514,576 | 7/1950 | Hein et al. | 604/212 |
| 3,199,510 | 8/1965 | Sinai | 128/66 |
| 3,368,280 | 2/1968 | Friedman et al. | 433/86 |
| 3,391,696 | 7/1968 | Woodward | 433/89 |
| 4,110,908 | 9/1978 | Cranston | 433/143 X |
| 4,276,880 | 7/1981 | Malmin | 433/80 X |
| 4,300,555 | 11/1987 | Kopito | 604/212 |
| 4,512,769 | 4/1985 | Kozam et al. | 433/80 X |
| 4,575,375 | 3/1986 | Kozam | 604/185 |
| 4,592,728 | 6/1986 | Davis | 433/81 X |
| 4,787,845 | 11/1988 | Valentine | 433/88 |
| 4,787,847 | 11/1988 | Martin et al. | 433/119 |

FOREIGN PATENT DOCUMENTS 7905465 1/1981 Netherlands ............... 128/66

Primary Examiner—Robert P. Swiatek
Assistant Examiner—Nicholas D. Lucchesi

[57] ABSTRACT

An improved hand-held syringe for convenient and safe self-use simultaneously scraping and irrigating periodontal pockets, featuring three elements:

a rubber-like bulb-syringe to carry medicant; a cannula whose distal end comprises both an aperture for dispensing the medicant and an irregular surface for scraping plaque; and, a tubular coupler comprising a smooth end for adjustable tight-fit insertion into an aperture in the bulb-syringe, the other end a (female) luer-lock with mates with a (male) luer-lock on the proximal end of the cannula.

1 Claim, 1 Drawing Sheet

APPARATUS AND METHOD FOR IRRIGATING AND ASPIRATING PERIODONTAL POCKETS

BACKGROUND OF INVENTION

The problem of periodontal pockets develops generally due to food debris getting caught between the teeth and calcification of the bacterial plaque develops when the food debris hasn't been cleaned out properly by methods such as the use of dental floss, toothbrushing or pulsating water devices.

The inability to clean the pockets properly can lead to further deepening of the pockets and eventually to tooth loss. Possibly, this can be corrected by periodontal surgery for a time, but eventually the condition may return without continued home care. In addition, this is a very expensive procedure and may discourage the patient in continuing professional periodontal care.

By way of the background, it is widely accepted that once the tissues surrounding a tooth has developed periodontal pockets, it is advisable to scrape and irrigate the pockets with various medicinal solutions to debride the root and tooth area of bacterial matter in an effort not to lose the tooth.

Prior art devices for scraping and irrigating body cavities commonly use syringe and cannula, however, the major problem is these are inconvenient for hand held self-use at home by the patient alone, to treat periodontal pockets. This major problem is answered by the present invention.

It is believed that none of the prior art will accomplish the purpose of the invention in as simplified and easy a manner as the present invention. Thus, it is an object of this invention to provide an improved method to cleanse and treat periodontal pockets by scraping, irrigating, and aspirating debris in the periodontal pocket area.

PRIOR ARTS REFERENCES CITED

There are several prior known devices and methods for dental treatment which generally include scraping and applying a fluid to the gums, although none of them disclose the present invention. Exemplary are these U.S. Patent Documents:

MALMIN No. 4,276,880; discloses a device possessing the capability of providing both irrigation and suction, however, this device must be used with a medicant dispensing tubular piston syringe which primarily was designed for professional use by the Dentist in debriding and irrigation of root canal therapy.

KAZAM No. 5,575,373; discloses a periopocket irrigating and treatment system that is a complicated mechanical device propelled by a ratchet wheel that is enclosed in a box-like device.

WOOSTEN & RIVES No. 3,860,000; this apparatus does not concern the teeth or mouth, but does indicate the ability of using a bulb-like pumping device to aspirate and irrigate.

Applicant is also aware of other needle-like devices in the patent prior art.

SUMMARY OF THE INVENTION

Specifically, this invention is an improved method and apparatus for scraping, irrigating, and aspirating periodontal pockets. The apparatus features an adjustable three piece assembly which allows convenient and safe one-handed self-use for simultaneous scraping and irrigation with germicidal liquids, gels or slurries.

The three piece assembly consists of a rubber-like bulb syringe, into which the smooth end of a tubular coupler is inserted, the other end with a luer-lock to hold a cannula whose terminal (distal) end has both an irregular surface and a small aperture to allow simultaneous scraping and irrigating of the periodontal pocket. The coupler luer-lock (after the cannula is removed) provides a larger aperture to aspirate medicant to fill the bulb, or to apply viscous gels or slurries. The smooth end of the tubular coupler is tight-fit in the bulb aperture, but shiftable for adjustment of appartus size and configuration. The bulb has a flat portion to rest standing.

DETAILED DESCRIPTION OF THE PREFERRED EMBODIMENT

Figure 1:
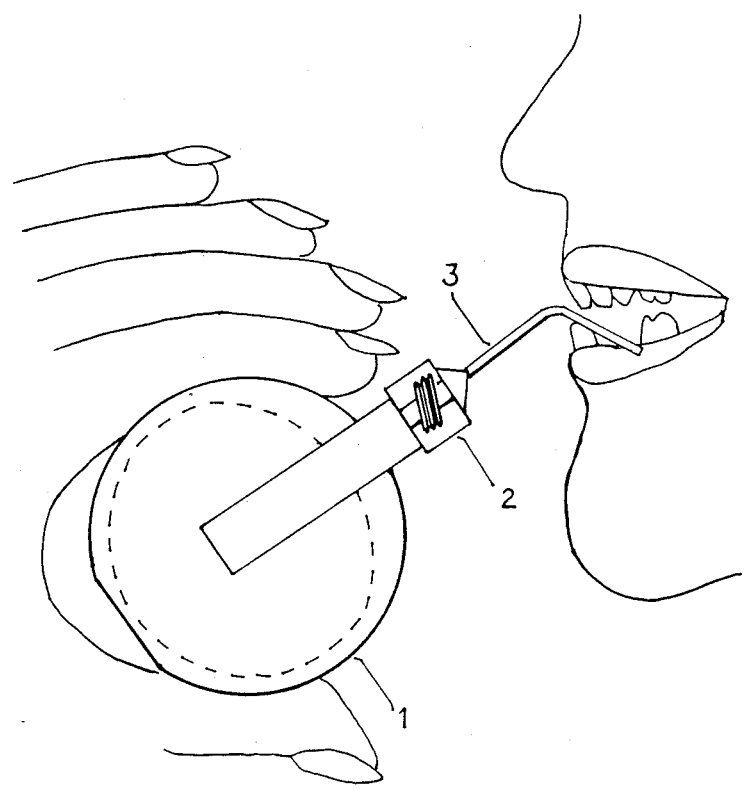
FIG. 1: Shows the apparatus and method of use.

Referring to FIG. 1, the apparatus is shown to consist of 3 parts: A bulb for carrying medicant (1); a coupler (2), and a cannula (3). The coupler consists of a tube, with one smooth end open for insertion into a bulb aperture, and the other end a luer-lock connector to attach the cannula.

In FIG. 1, the apparatus is shown in use: The bulb is a syringe held and squeezed by the patient's hand, forcing medicant contained therein to be forced through the tubular coupling and cannula into the periodontal pocket. Note that in the method of use the tubular coupler is shifted more or less into the bulb for adjustment of optimal apparatus size and configuration.

The cannula is bent at approximately a 45 degree angle for convenient insertion into the mouth and the periodontal pocket.

The surface of the distal end of the cannula can be serrated or scored slightly to assist in the scraping removal of plaque.

Fluid medicants are applied through the narrow aperture of the cannula. Viscous substances such as gels and slurries are better applied through the larger aperture of the tubular coupling luer-lock.

The bulb, of rubber or equivalent plastic is a size conveniently hand held and of a flexible rigidity to support moderate insertion forces without collapse. The bulb may be filled by aspiration more conveniently by the removal of the cannula to use the larger aperture of the coupler luer-lock and/or the tubular coupler.

What I claim is:

1. A method of treatment of a periodontal pocket by a self-user, using a hand-held apparatus comprising a coupler which adjustably couples a bulb-syringe to a cannula, the coupler comprising a tube with one end smooth which allows a tight adjustable slip-fit into an aperture in the bulb-syringe, the other end of the tube has a female luer-lock which connects to a male luer-lock at one end of the cannula, the other end of the cannula comprising both an aperture for dispensing medicant and an irregular surface for scraping, the method comprising:
   (a) adjusting the coupler for an amount of insertion for optimal size and configuration of the apparatus for convenient and safe use by the self-user;
   (b) removing the cannula to allow aspirating fluid medicant through the aperture of the coupler luer-lock which provides a larger aperture than the relatively small dispensing aperture of the cannula;

(c) aspirating medicant through the coupler luer-lock aperture into the bulb-syringe;

(d) replacing the cannula;

(e) treating the periodontal pocket by hand-squeezing the, bulb-syringe to expel irrigating medicant, while simultaneously hand-vibrating the bulb-syringe to force the cannula to scrape wall matter such as plaque in the periodontal pocket;

(f) removing the cannula from the apparatus to allow emptying more quickly the bulb-syringe of fluid medicant;

(g) aspirating viscous medicant through the coupler luer-lock aperture into the bulb-syringe;

(h) applying the viscous medicant by hand-squeezing the bulb-syringe to force viscous medicant through the luer-lock aperture into and about the periodontal pocket; and (i) resting the device on a flat-portion of the bulb-syringe when not in use.

* * * * *